(12) United States Patent
Papay et al.

(10) Patent No.: US 6,800,087 B2
(45) Date of Patent: Oct. 5, 2004

(54) BLANKET SYSTEM FOR TEMPERATURE REGULATION OF A PATIENT

(75) Inventors: Francis A. Papay, Westlake, OH (US); Stefan Budac, San Antonio, TX (US)

(73) Assignee: The Cleveland Clinic Foundation, Cleveland, OH (US)

( * ) Notice: Subject to any disclaimer, the term of this patent is extended or adjusted under 35 U.S.C. 154(b) by 165 days.

(21) Appl. No.: 10/182,170

(22) PCT Filed: Jan. 5, 2001

(86) PCT No.: PCT/US01/00285
§ 371 (c)(1),
(2), (4) Date: Oct. 3, 2002

(87) PCT Pub. No.: WO01/50988
PCT Pub. Date: Jul. 19, 2001

(65) Prior Publication Data
US 2003/0208251 A1 Nov. 6, 2003

Related U.S. Application Data
(60) Provisional application No. 60/174,944, filed on Jan. 7, 2000.

(51) Int. Cl.$^7$ .................................................. A61F 7/00
(52) U.S. Cl. ........................ 607/104; 607/107; 607/108; 607/109; 607/110; 607/111
(58) Field of Search ................................. 607/104, 107, 607/108, 109, 110, 111

(56) References Cited

U.S. PATENT DOCUMENTS

| | | | |
|---|---|---|---|
| 3,757,366 A | 9/1973 | Sacher | |
| 5,025,777 A | 6/1991 | Hardwick | |
| 5,683,438 A | * 11/1997 | Grahn | ........................ 607/104 |
| 5,735,890 A | 4/1998 | Kappel et al. | |
| 5,966,763 A | 10/1999 | Thomas et al. | |
| 6,197,045 B1 | * 3/2001 | Carson | ........................ 607/104 |

* cited by examiner

Primary Examiner—Michael Peffley
Assistant Examiner—Aaron Roane
(74) Attorney, Agent, or Firm—Tarolli, Sundheim, Covell & Tummino L.L.P.

(57) ABSTRACT

A blanket system (1) is provided for maintaining or controlling a patient's body temperature before, during, or after surgical and non-surgical procedures. The system includes a non-obtrusive cover blanket (3), a blower (28) to blow the air beneath the blanket (3) and a vacuum source (30) to suction the air from beneath the blanket (3) and away from the patient.

11 Claims, 6 Drawing Sheets

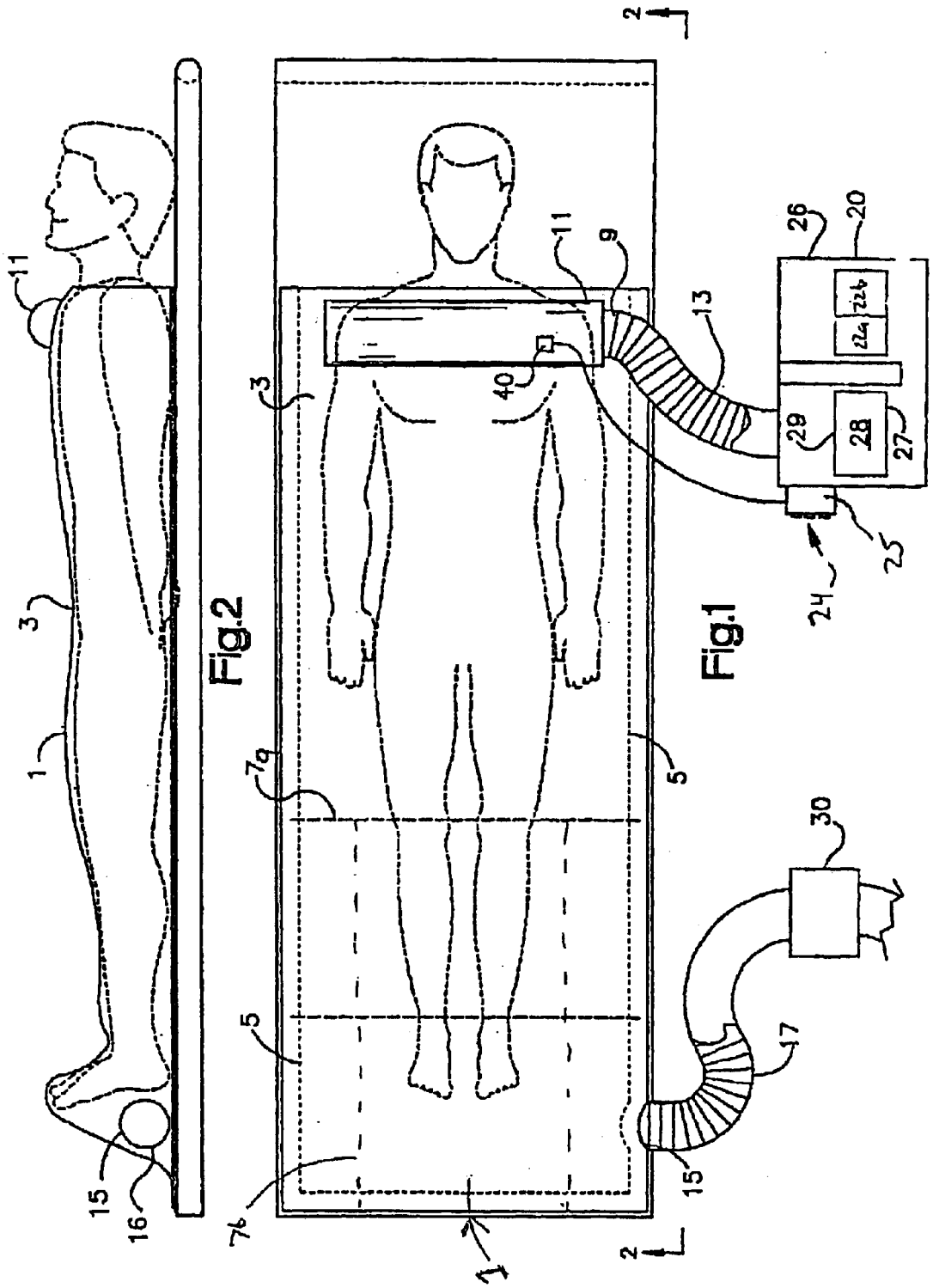

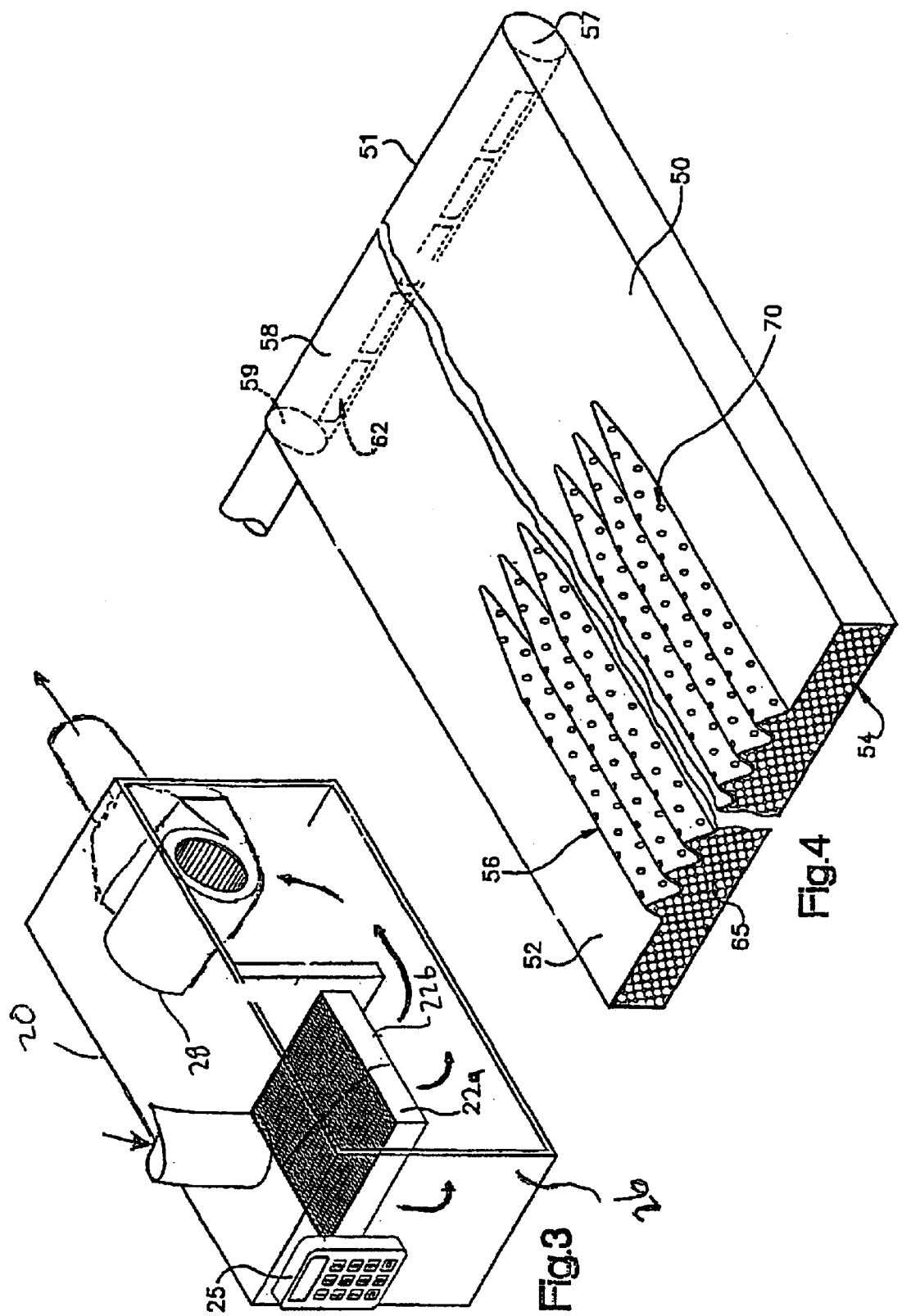

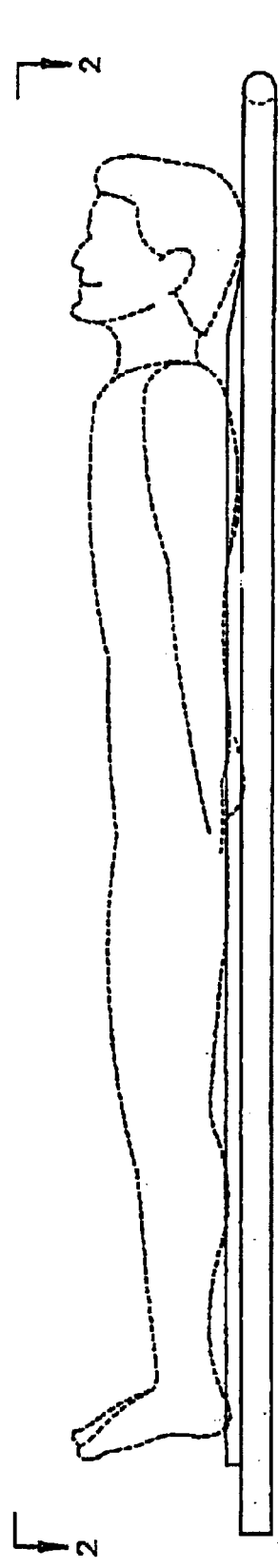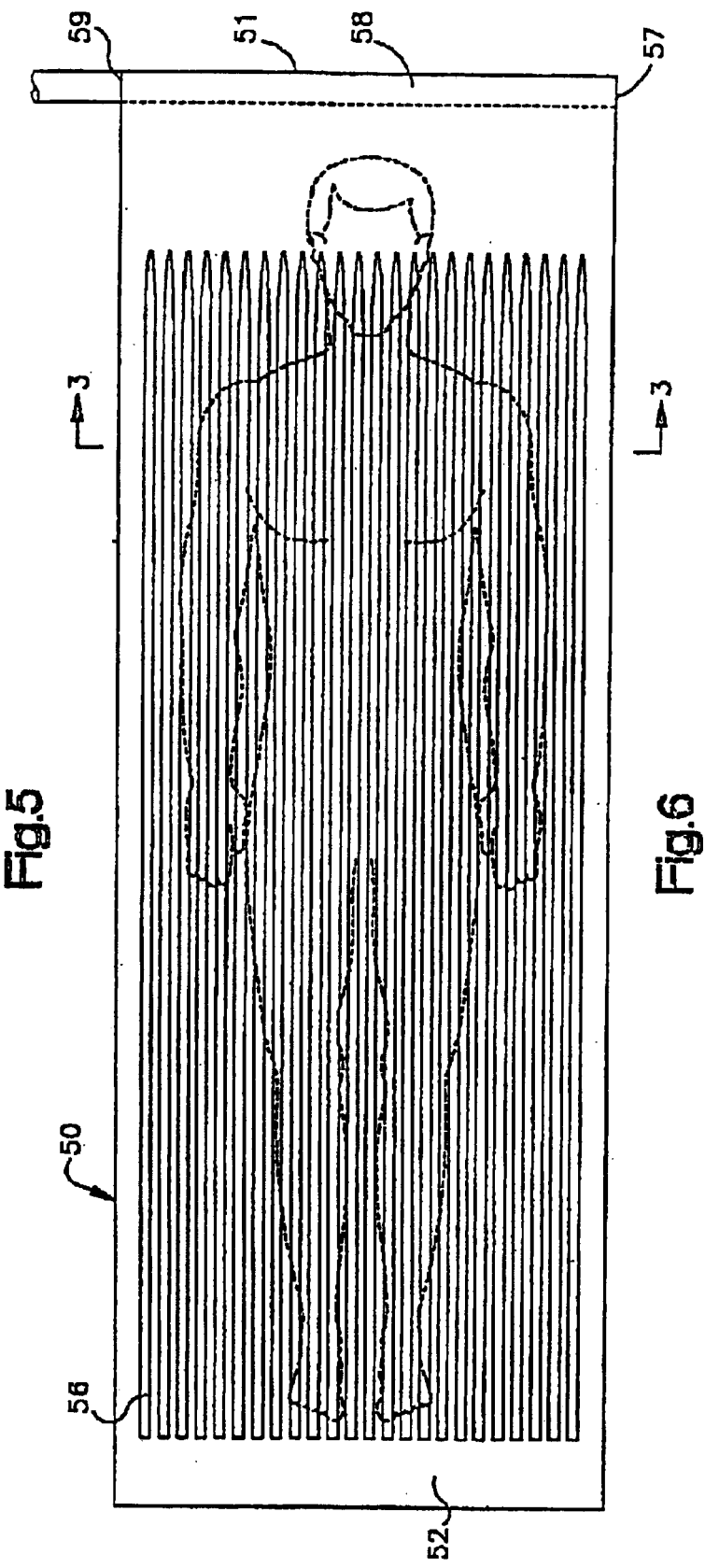

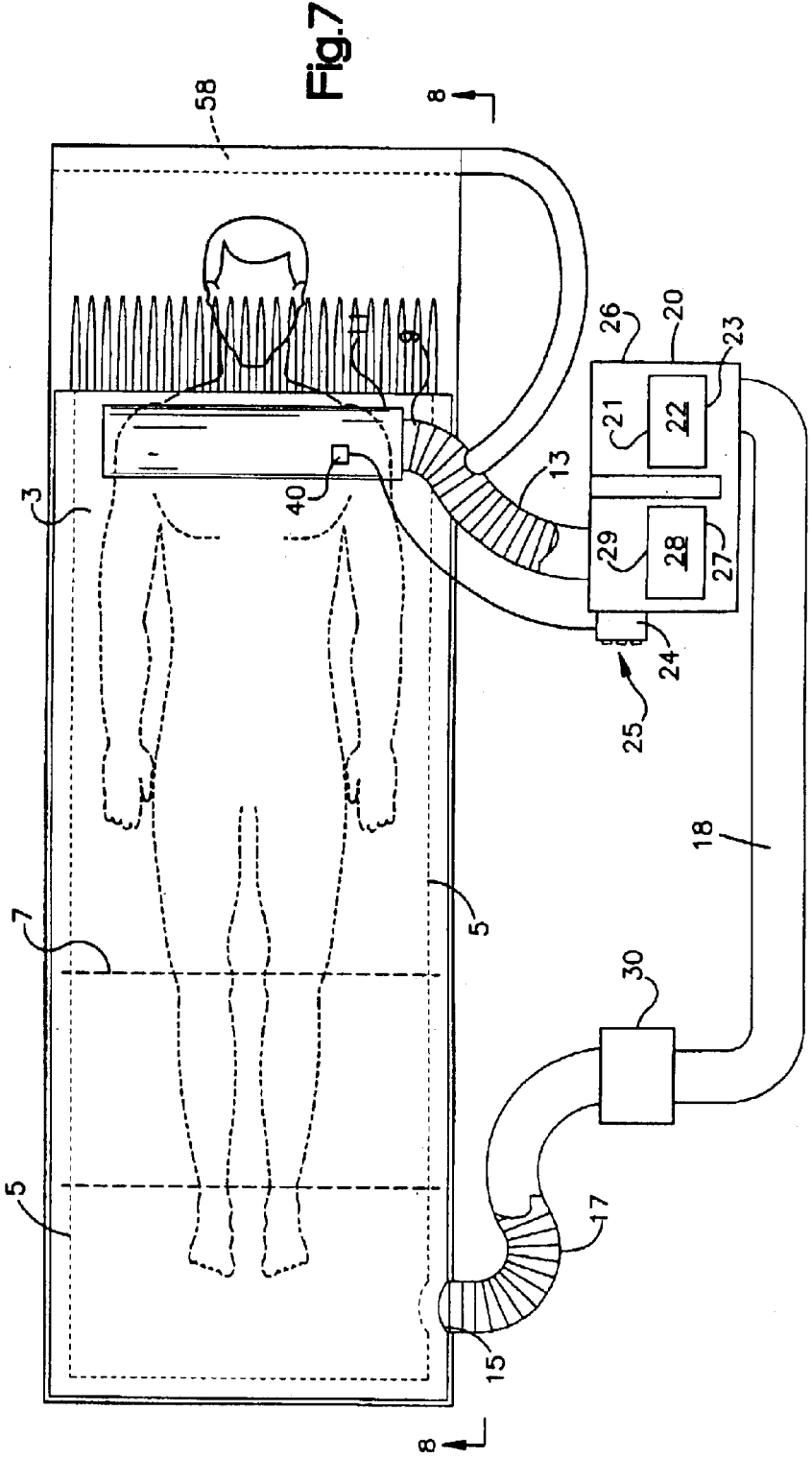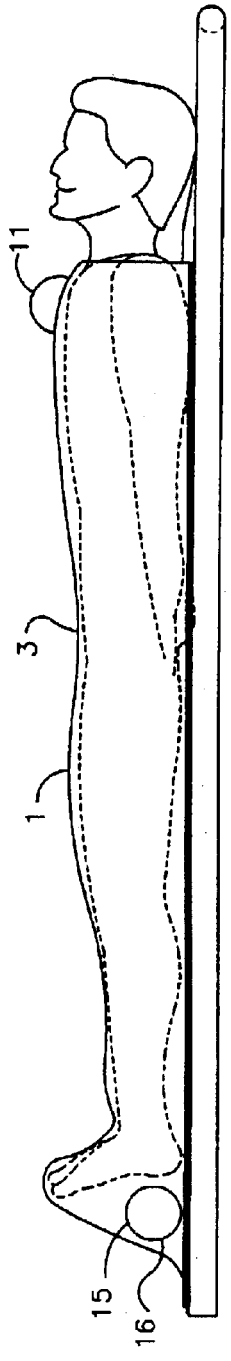

BLANKET SYSTEM FOR TEMPERATURE REGULATION OF A PATIENT

This application claims the benefit of Provisional Application No. 60/174,944 filed Jan. 7, 2000.

FIELD OF THE INVENTION

This invention generally relates to a thermal blanket and more specifically to a device and method for regulating the body temperature of a patient.

BACKGROUND OF THE INVENTION

The control of body temperature of patients is particularly a concern before, during and after surgical operations because an abnormal temperature may affect the stability of the patient under anesthesia as well as the patient's recovery. One significant issue concerning the control of the patient's body temperature is hypothermia. Hypothermia in turn leads to complications during and after surgery including: thermal discomfort, impairment of the blood's ability to coagulate, impaired response by the body to wound infections and in serious situations even congestive heart failure, respiratory failure, or stroke. Loss of heat from the patient can be caused by a variety of factors including: the low temperature of the operating room, lack of insulating clothing on the patient, preparation of the patient's skin using cold or volatile solutions, and losses from incisions made upon the patient. The problem is compounded by the increased difficulty of the patient's body to thermoregulate itself during an operation because of the effects of anesthesia. The restoration of normal body temperature is also a concern for patients suffering from hypothermia due to overexposure to cold conditions unrelated to surgery. Thus it is important to warm up the patient as quickly as possible. Conversely, patients who are hyperthermic may require medical intervention to reduce their body temperature to prevent damage to internal organs.

Many solutions have been proposed to minimize heat loss from patients. Some include introducing heat to the patient from an outside source such as the application of prewarmed hospital blankets. This is an inexpensive, simple solution, but has the disadvantage in that the blankets are merely insulators and the heat introduced by prewarming is quickly dissipated. Blankets which have heated water circulating throughout have also been used with some degree of success. These blankets have an outside source of heat, but are generally heavy and bulky due to the fluid's weight. Water blankets can also be unsanitary because they are used repeatedly and have a tendency to leak over time.

Another prior art approach to controlling the patient's body temperature is to increase the operating room temperature or at least the area around the patient using heat lamps. This method has the drawback of overheating of the surgical team which is generally heavily clothed already.

Another approach to regulating patient temperature is through utilization of air circulating blankets and cushions which provide an outside source of heat. One disadvantage of this approach is that dual walled blankets which have an interior chamber for air passage are a physical obstruction due to their inherent thickness. When air is supplied to the blanket, the blanket "puffs up" and may interfere with surgery. If the interior chamber is instead a series of passages, it is difficult to reduce the overall size of the blanket or cut access holes into it without eliminating air flow within an entire passage. Also, prior art air circulating blankets or blanket systems exhaust the heated air around the patient, which then results in overheating of the surgical team.

A system having the ability to supply air which will warm or cool a patient and the ability to suction air away from the area around the patient, and which is not obtrusive is desired.

SUMMARY OF THE INVENTION

The present invention overcomes these and other disadvantages of the prior art by providing a system which uses a thin, non-obtrusive cover blanket underneath which, air is introduced. The invention provides in one aspect, a surgical blanket system for regulating a patient's temperature comprising a blanket, a source of air including a blower which blows said air beneath said blanket at a first end, and a vacuum source which suctions said air from beneath said blanket at a second end.

The invention provides in another aspect a device for regulating a patient's temperature comprising a support cushion having upper and lower spaced surfaces which define an interior chamber containing heat retaining material, said upper surface having one or more holes, and a source of air, connected to an inlet of said interior chamber.

The invention provides in yet another aspect a surgical blanket system for regulating a patient's temperature comprising a blanket, a source of air including a blower which blows said air beneath said blanket at a first end, and a vacuum source which suctions said air from beneath said blanket at a second end, as well as a support cushion having upper and lower spaced surfaces which define an interior chamber containing heat retaining material, said upper surface having one or more holes, and a source of air connected to an inlet of said interior chamber.

The invention provides in yet another aspect a method for controlling the temperature of a patient comprising the steps of: covering a portion of the patient with a blanket, forcing air from an air source beneath said blanket using a blower, and suctioning air from underneath said blanket using a vacuum source.

These and other aspects of the invention are herein described in particularized detail with reference to the accompanying Figures.

BRIEF DESCRIPTION OF THE FIGURES

FIG. 1 is a top view of a blanket system with a patient lying on an operating table beneath the cover blanket;

FIG. 2 is a side view of the cover blanket covering a patient lying upon an operating table;

FIG. 3 is a perspective view of the source of air;

FIG. 4 is a perspective view of the support cushion;

FIG. 5 is a side view of a patient lying upon the support cushion;

FIG. 6 is a top view of a patient lying upon the support cushion;

FIG. 7 is a top view of the blanket system being used in conjunction with the support cushion;

FIG. 8 is a side view of the blanket system being used in conjunction with the support cushion;

DETAILED DESCRIPTION OF PREFERRED AND ALTERNATE EMBODIMENTS

Figure 9:
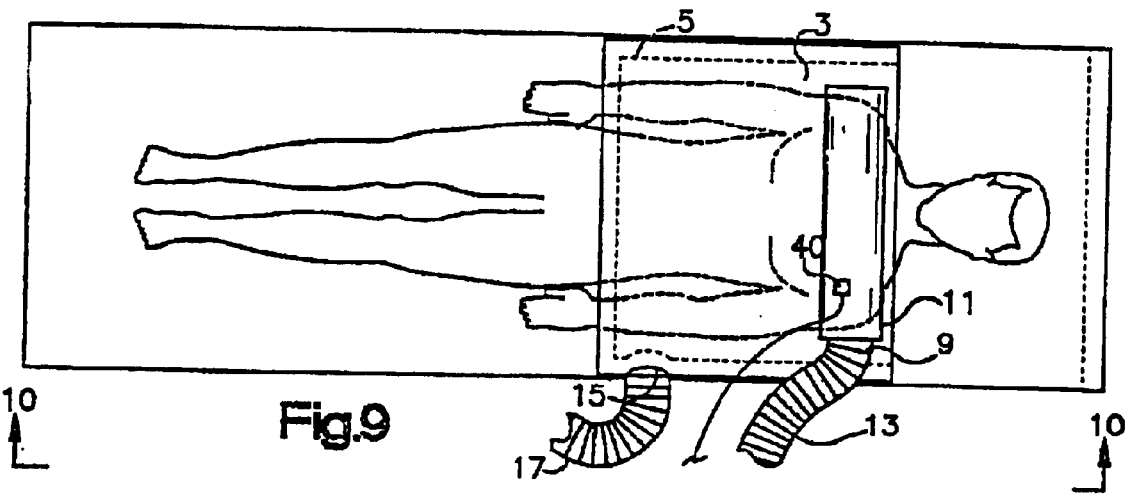
FIG. 9 is a top view of a modified blanket system where sections of the blanket have been removed to allow surgical access to the lower body.
Figure 10:
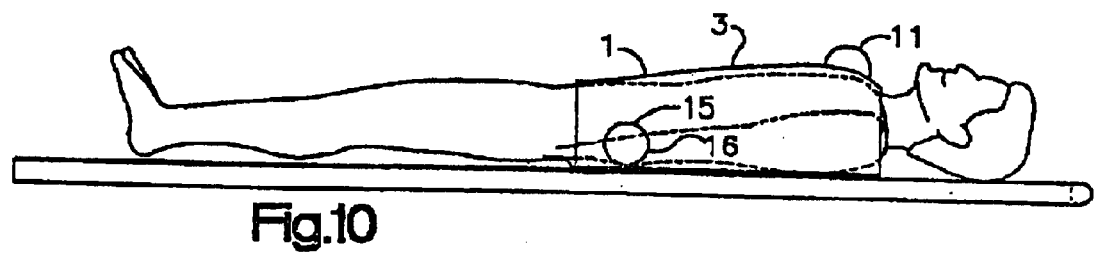
FIG. 10 is a side view of a modified blanket system where sections of the blanket have been removed to allow surgical access to the lower body.
Figure 11:
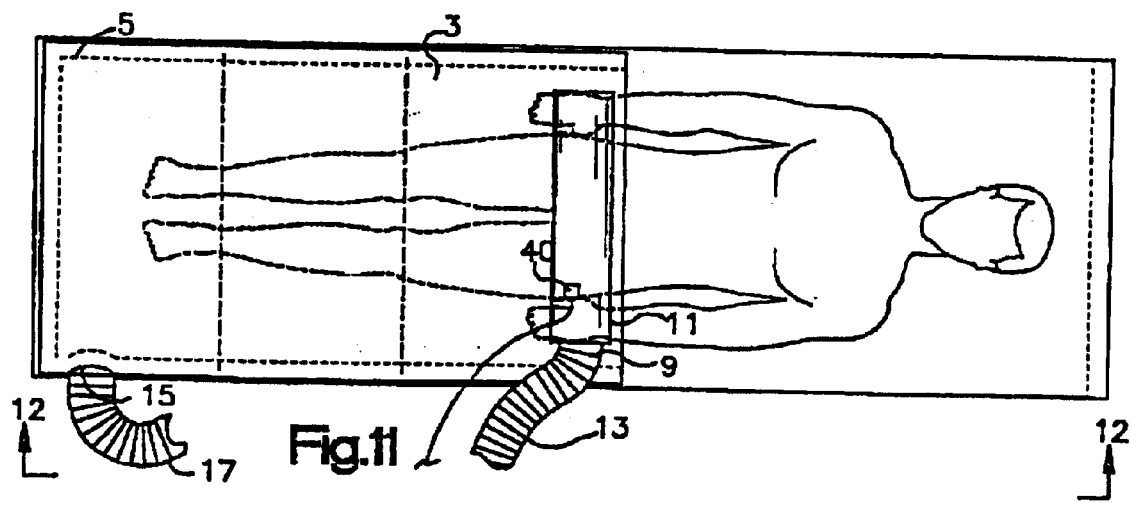
FIG. 11 is a top view of a modified blanket system where sections of the blanket have been removed to allow surgical access to the upper body.
Figure 12:
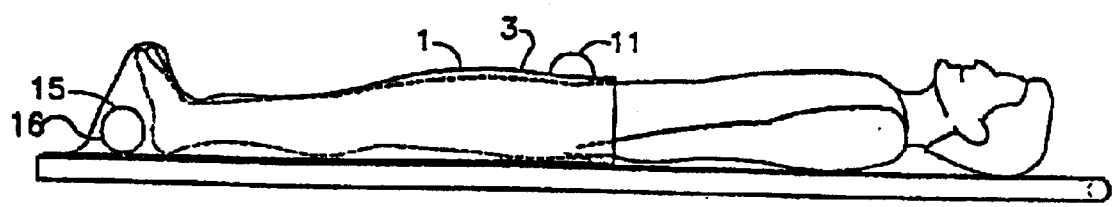
FIG. 12 is a side view of a modified blanket system where sections of the blanket have been removed to allow surgical access to the upper body.
Figure 13:
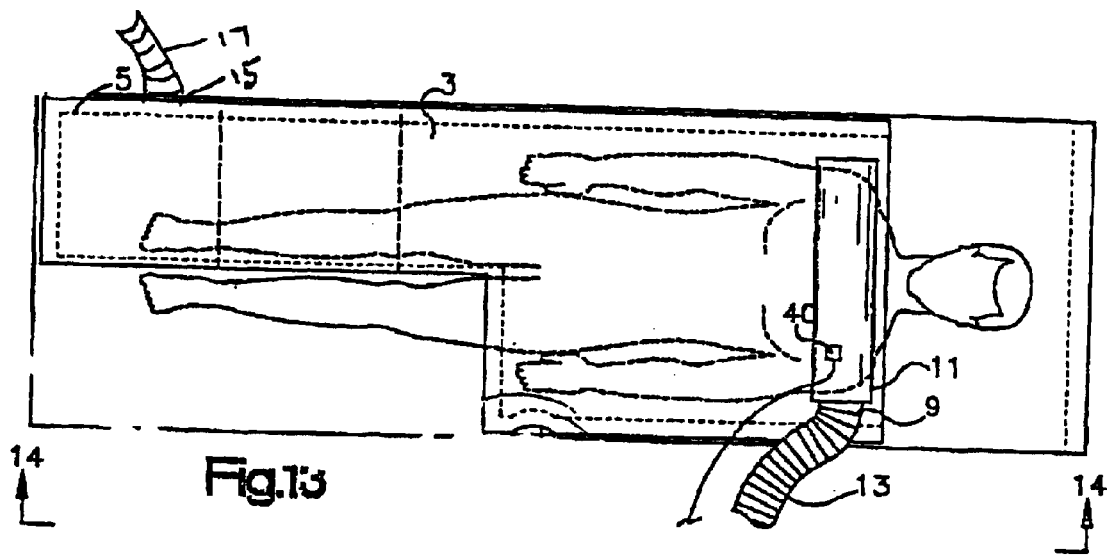
FIG. 13 is a top view of a modified blanket system where sections of the blanket have been removed to allow surgical access to a single leg.
Figure 14:
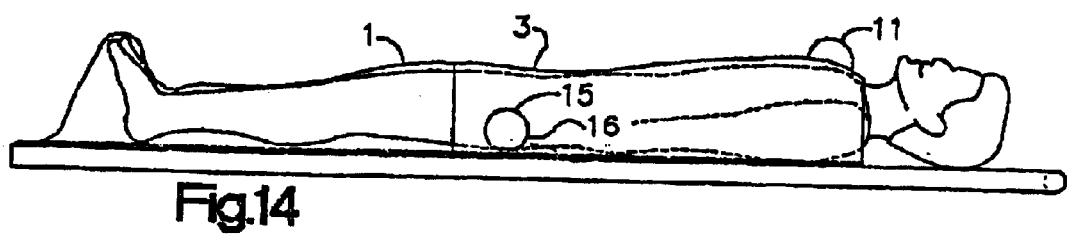
FIG. 14 is a side view of a modified blanket system where sections of the blanket have been removed to allow surgical access to a single leg.

Referring to the drawings, FIG. 1 illustrates a preferred blanket system 1 according to the invention. This blanket system 1 may be used to regulate the temperature of a patient for example, before, during and after surgery. Alternatively, the system may be used in non-surgical situations where it is necessary to raise or lower a patient's temperature. The blanket system, as described in more detail below, comprises a cover blanket 3, a source of air 20, and a vacuum source 30 to suction and exhaust the air from under the blanket 3 after it has passed over the patient. Either warmed, cooled or room temperature air may be supplied from the source of air 20 depending upon the required treatment to the patient. The cover blanket 3 is preferably sized so it fits over a patient's chest, torso, legs and feet. Alternatively, the size of the blanket may be reduced to cover only a portion or portions of the body. FIGS. 9–16 show variations in the size of the cover blanket 3, for example covering a patient's body from the feet to the torso or from the patients neck to the torso. Cover blanket 3 is of sufficient width to completely cover the patient. The cover blanket 3 is preferably made of paper which may be disposed of after each use. Alternatively, the blanket may be made of cloth or plastic or any other material which results in a blanket which is thin, non-obtrusive and preferably inexpensive.

Figure 15:
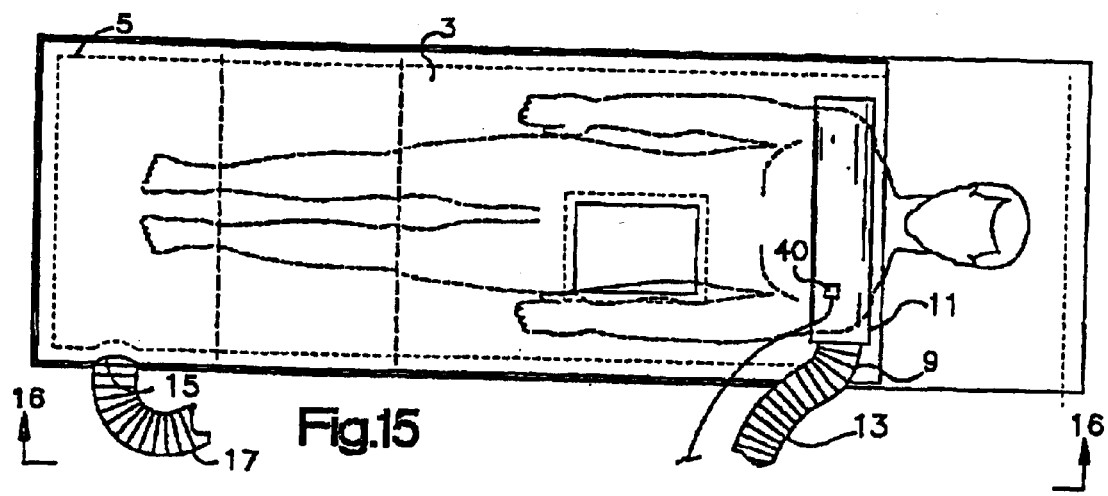
FIG. 15 is a top view of a modified blanket system where a hole has been cut out of the cover blanket and the blanket sealed to the patient's body to allow surgical access to the center of the body and FIG. 16 is a top view of a modified blanket system where a hole has been cut out of the cover blanket and the blanket sealed to the patient's body to allow surgical access to the center of the body.
Figure 16:
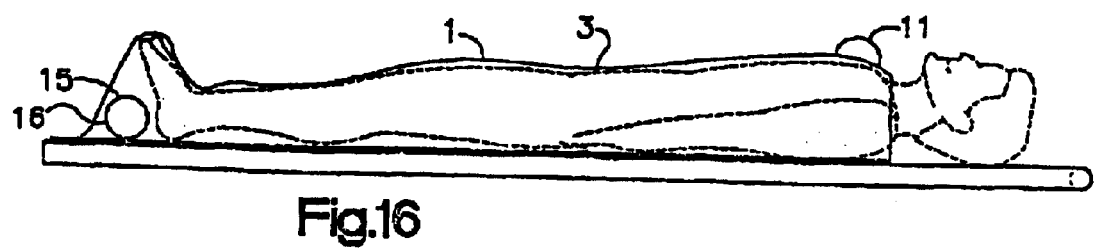

Cover blanket 3 is preferably equipped with double sided tape 5 to attach it to another surface, such as an operating table. Instead of tape, other attachment means may be used such as two part cloth adhering strip systems, an adhesive strip, or other means known to those skilled in the art. The tape 5 is placed along the outside perimeter of the blanket 3. Preferably, the tape 5 is applied to the blanket in such a way as to allow an air tight seal to be formed between blanket 3 and a lower surface. Cover blanket 3 may be attached directly to the patient using tape or other adhesive in areas of the perimeter which do not contact the operating table. Cover blanket 3 may preferably comprise one or more horizontal or vertical seams 7 which are created by a perforation process. These seams allow for quick removal of a part of the blanket 3 when a smaller blanket is preferred. For example, reduced size may be required when the surgery is to take place on a lower part of the body as shown in FIG. 9. Cover blanket may also be cut using a knife or scissors when small areas of the body must be exposed as shown in FIG. 15. Preferably the perimeter of any cut area still be secured to the body or the lower surface using tape 5 in order to keep the air beneath the cover blanket 3.

Blanket system 1 further includes a source of air 20 which comprises a blower 28 and is used in conjunction with an inlet port 9 and diffuser 11, an air supply duct 13, and a heating and/or cooling element 22. The element 22 heats air from the source of air 20 when room temperature air is insufficient to warm the patient. The element 22 cools the air from the source of air 20 when room temperature is insufficient to cool the patient. An inlet port 9 allows air to be blows beneath the cover blanket 3. A diffuser 11 is preferably integrally formed with the inlet port 9, but may also be a separate connected piece. Diffuser 11 is used to spread air evenly along the width of the blanket. While any size or shape of the diffuser 11 may be utilized, it is preferred that the diffuser 11 is elongated and rectangular shaped, having multiple discharge ports which allow an equal amount of air to exit along its length. Preferably, the diffuser 11 is positioned close to the edge of cover blanket 3 near the patient's head. Alternatively, placement may be in the chest or torso region. Air is brought to the inlet port 9 and diffuser 11 via an air duct 13 which is connected to the inlet port 9 as well as a source of air 20.

Referring to FIG. 3, a system to blow air is shown. Air source 20 comprises a blower 28 to transfer air through air duct 13. Preferably, the blower and the heating/cooling element 22 are held within case 26. Preferably the heating/cooling element 22 are sized to generate a constant supply of air in a temperature range of about 35 to 45 degrees Centigrade. Depending upon the size of heating/cooling element 22, and blower 28, these elements may be aligned side by side or in line within case 26, but are not limited to these positions.

In an embodiment including healing/cooling element 22, preferably a temperature control system 24 is used to maintain the air within a preset temperature range. The temperature control system 24 includes one or more temperature sensors 40 as shown in FIG. 1. The temperature sensor 40 may be a thermocouple or other type of sensor known to those skilled in the art. The temperature sensor 40 may be utilized to monitor the temperature of the patient at various places, and the inlet air stream temperature near the patient. The control system also includes a dial or other device 25 known to those skilled in the art where a desired temperature range can be set. The control system is connecting to the heating/cooling element 22, and the blower to cycle the elements and blower in order to achieve a temperature in the range of about 35 to 45 degrees Centigrade. Temperature sensor 40 may be used in a system not utilizing a heating/cooling element 22 to simply monitor air temperature.

The blanket system 1 further comprises a vacuum source 30 to suction air from beneath the cover blanket 3. Vacuum source 30 may be a blower or other device known in the art which creates suction. FIGS. 1 and 2 show a suction port 15 placed in an area preferably distant from the diffuser 11. Preferably suction port 15 is a fixture, made of an inexpensive material attached around a hole 16 in blanket 3. However, suction port 15 may be the same element as air duct 17 which is a simple tube or other type of air duct and is placed through blanket 3 or between blanket 3 and the surgical table with blanket 3 being taped to the tube. This port allows air which has passed across the body of the patient to be exhausted to an area away, from the surgical staff. Thus the staff is not inconvenienced by extra heat or air motion and this is an advantage that did not exist in the prior art. If suction port 15 is not the same element as air duct 17, suction port 15 is connected to air duct 17. Suction is created within air duct 17 by use of a vacuum source 30 with the intake end preferably being sealed to the air duct 17. Preferably the flowrate of the vacuum source 30 is about the same as the flowrate of air blower 28. Preferably, exhaust air may be used as supply air for blower 28. This increases energy efficiency in systems utilizing a heating/cooling element 22. As shown in FIG. 7 auxiliary air duct 18 may route air to blower 28, heating/cooling element 22. Alternatively, exhaust air may be dumped to an area away from the surgical staff.

The operation of the system may now be described. In an embodiment using either heating/cooling element 22, supply air from the general surroundings is suctioned into the inlet side of heating/cooling element 22. Supply, air passes through heating/cooling element 22. This supply air, now in the desired temperature range, passes into the inlet side 27 of the blower 28. In an embodiment without heating/cooling element 22, supply air is suctioned directly into the inlet side 27 of blower 28. Supply air then passes through the outlet side 29 of the blower and into air duct 13. After passing through the air duct 13, the air reaches the diffuser 11 and is discharged across the body of the patient. As it reaches the lower end of the patient the air is sucked away through the suction port 15, through air duct 17, to the vacuum source 30. Preferably, the air from vacuum source 30 is routed back through auxiliary duct 17 to the heating/cooling element 22 or blower 28. Alternatively the air is discharged in an area away from the surgical team.

In an alternate embodiment of the invention, a support cushion 50 is shows in FIG. 4. The support cushion 50 may be used alone or in conjunction with the blanket system 1. Support cushion 50 is sized and shaped for placement upon a common operating table and configured for placement underneath a patient. As shows in FIG. 4, cushion 50 has an upper surface 52 and a lower surface 54 which are spaced apart creating a chamber within. Preferably, a portion of the upper surface 52 has one or more channels 56 oriented lengthwise. Channels 56 allow for greater heat transfer by convection of the air through the cushion 50 and to the patient. Further, channels 56 create a place for fluids to pool so that they do not contact the patient. Preferably the perimeter of the upper surface is smooth thus allowing a cover blanket to be easily attached to the surface as shown in FIG. 6. Upper surface 52 contains multiple holes 70 which allow the passage of air from the cushion chamber to the area surrounding the patient.

The operation of the support cushion max now be described. Air is blown into a first end 51 of the cushion 50. Preferably a plenum 58 is used to distribute the air along the entire width of the cushion 50. Plenum 58 is shown as a tubular piece extending the entire width of the cushion 50, but is not limited to this shape. Plenum 58 includes multiple holes 62 from which the air may enter the cushion chamber. One end 57 of plenum 58 is sealed while the opposite end 59 is open. A source of air ma be attached to opposite end 59 of the plenum 58. The source may be similar to air source 20 or could be the same source if the cushion 50 is used in conjunction with the blanket 1. The chamber of cushion 50 is filled with heat retaining material such as fibers. Preferably, the heat retaining material is beads 65 which may be made of Styrofoam or other material such as plastic so the cushion 50 will retain heat when the source of air is closed off. Preferably the beads 65 are of a spherical shape and size, which ill allow air to pass between them even when packed tightly together.

Air from within the cushion 50 passes through holes 70 in the upper surface 52 of the cushion and into the area around the patient. When the cushion 50 is used alone, this air escapes into the surroundings. When used in conjunction with blanket system 1, air from the cushion 50 is suctioned from under the cover blanket 3 by vacuum source 30.

The blanket system 1, cushion 50 or combination of both as shown in FIGS. 7 and 8 may be used to regulate a patient's temperature during an operation before an operation, during recover, and where temperature regulation of the patient is required. However, the invention is not limited to the above described uses on the invention.

Although the invention has been shows and described with reference to certain preferred and alternate embodiments the invention is not limited to these specific embodiments. Minor variations and insubstantial differences in the various combinations of materials and methods of application may occur to those of ordinary, skill in the art while remaining within the scope of the invention as clamed and equivalents.

What is claimed is:

1. A surgical blanket system for regulating a patient's temperature comprising:

a blanket having oppositely disposed first and second ends;

a source of air including a blower which blows said air beneath said first end of said blanket; and a vacuum source which suctions said air from beneath said blanket at said second end of said blanket.

2. The surgical blanket system according to claim 1, wherein said blanket includes double side tape along its perimeter for sealing said perimeter to another surface.

3. The surgical blanket system according to claim 1, further having perforated seams which divide said blanket into sections.

4. The surgical blanket system according to claim 1, further having a temperature control system which maintains said air within a range of about 35 to 45 degrees Centigrade.

5. The surgical blanket system of claim 1, wherein an outlet end of said vacuum source is connected to an intake of said blower.

6. The surgical blanket system according to claim 1 wherein said air is heated.

7. The surgical blanket system according to claim 1 wherein said air is cooled.

8. A surgical blanket system for regulating a patient's temperature comprising:

a blanket;

a source of air including a blower which blows said air beneath said blanket;

a vacuum source which suctions said air from beneath said blanket; and a support cushion having upper and lower spaced surfaces which define an interior chamber containing a heat retaining material;

said upper surface having one or more holes for directing airflow over the patient;

said source of air also introducing air into said interior chamber.

9. The surgical blanket system according to claim 8 wherein said heat retaining material is spherically shaped.

10. The surgical blanket system according to claim 8 wherein said heat retaining material is styrofoam.

11. A method of controlling the temperature of a patient comprising the steps of:

covering the patient with a blanket;

forcing air from an air source beneath said blanket using a blower; and suctioning air from underneath said blanket using a vacuum source.

* * * * *